/ 310-335
10/2/84    OR    4,475,054

United States Patent [19]
Baumoel

[11] Patent Number: 4,475,054
[45] Date of Patent: Oct. 2, 1984

[54] METAL TRANSDUCER HOUSING WITH FOCUSING SURFACE

[76] Inventor: Joseph Baumoel, 107 Columbia Dr., Jericho, N.Y. 11753

[21] Appl. No.: 542,691

[22] Filed: Oct. 17, 1983

[51] Int. Cl.³ .......................................... H01L 41/08
[52] U.S. Cl. .................................. 310/335; 310/336; 73/642
[58] Field of Search .............................. 310/334–337; 73/642, 644

[56] References Cited

U.S. PATENT DOCUMENTS

| | | | |
|---|---|---|---|
| 3,302,044 | 1/1967 | Lynnworth et al. | 310/336 X |
| 3,379,902 | 4/1968 | Harris et al. | 310/335 |
| 3,433,059 | 3/1969 | Cavalier | 310/336 X |
| 3,832,655 | 8/1974 | Yokoyama | 310/335 X |

Primary Examiner—Mark O. Budd
Attorney, Agent, or Firm—Ostrolenk, Faber, Gerb & Soffen

[57] ABSTRACT

The transducer housings for clamp-on transducers of a flowmeter system are cast of an aluminum zinc alloy which is sonically conductive after casting. The transducer housings have a shear mode converting surface which has a longitudinal curvature and a cross-curvature. The cross-curvature of the shear mode conversion surface defines a solid lens which tends to focus internally reflected shear mode converted energy along the line of intersection of the flat output surface of the transducer housing with a circular metal conduit. The longitudinal curvature of the shear mode converting surface adjusts the phase velocity over the transducer output surface so as to focus the beam and reduce beam spreading along the length of the pipe and generally to correct aperture dispersion. A relatively low Q transducer crystal assembly is coupled to the aluminum-zinc alloy housing.

12 Claims, 13 Drawing Figures

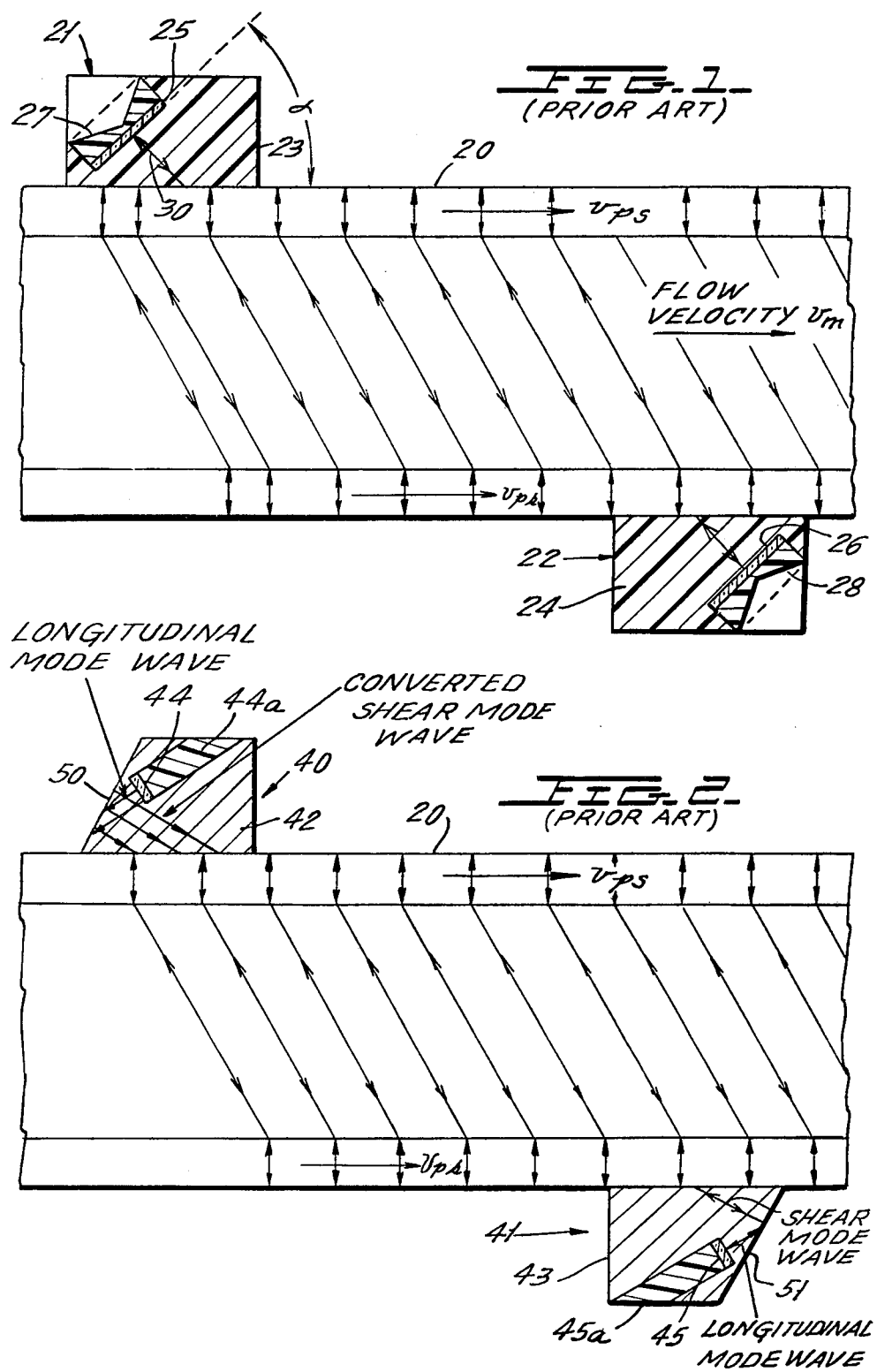

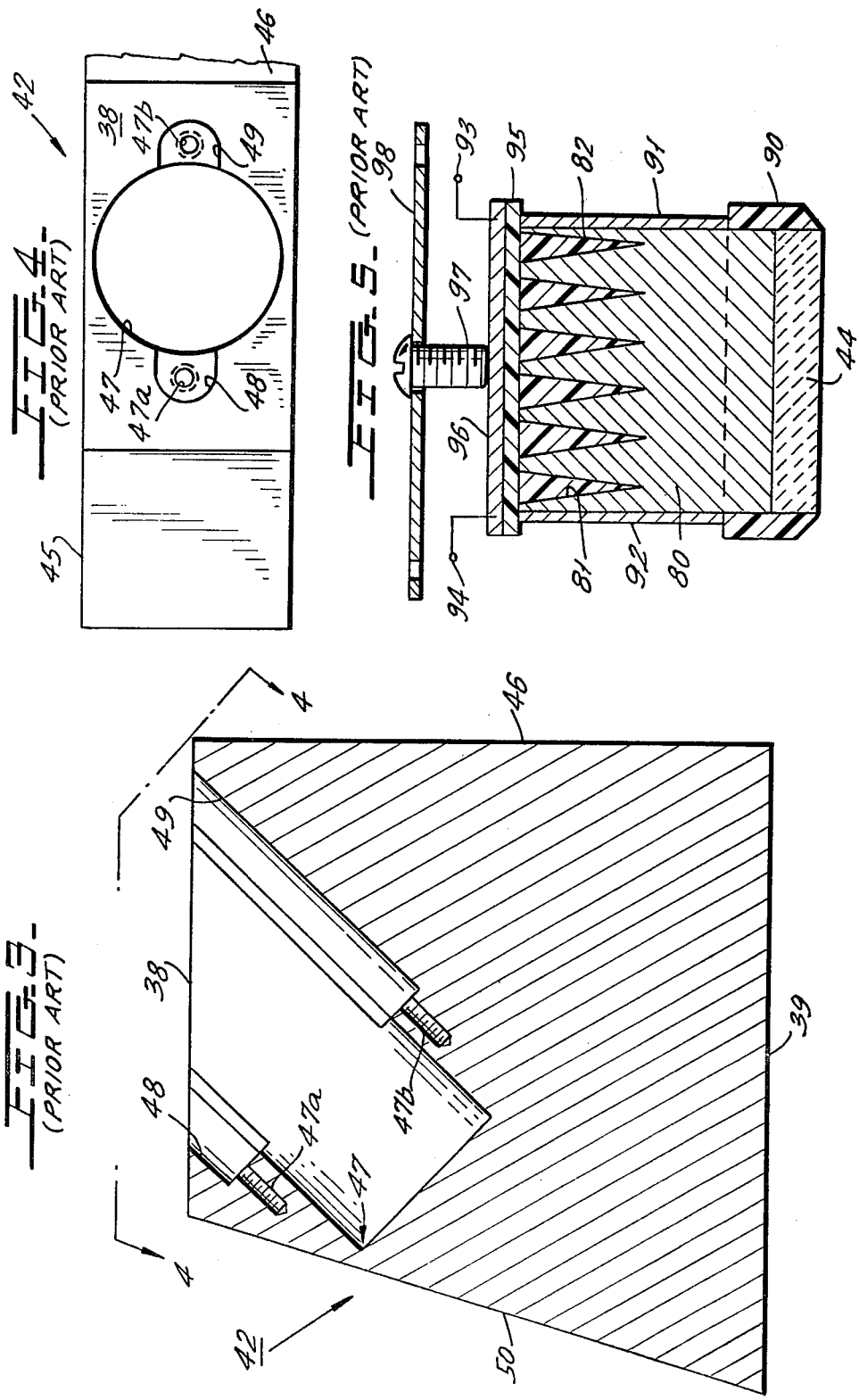

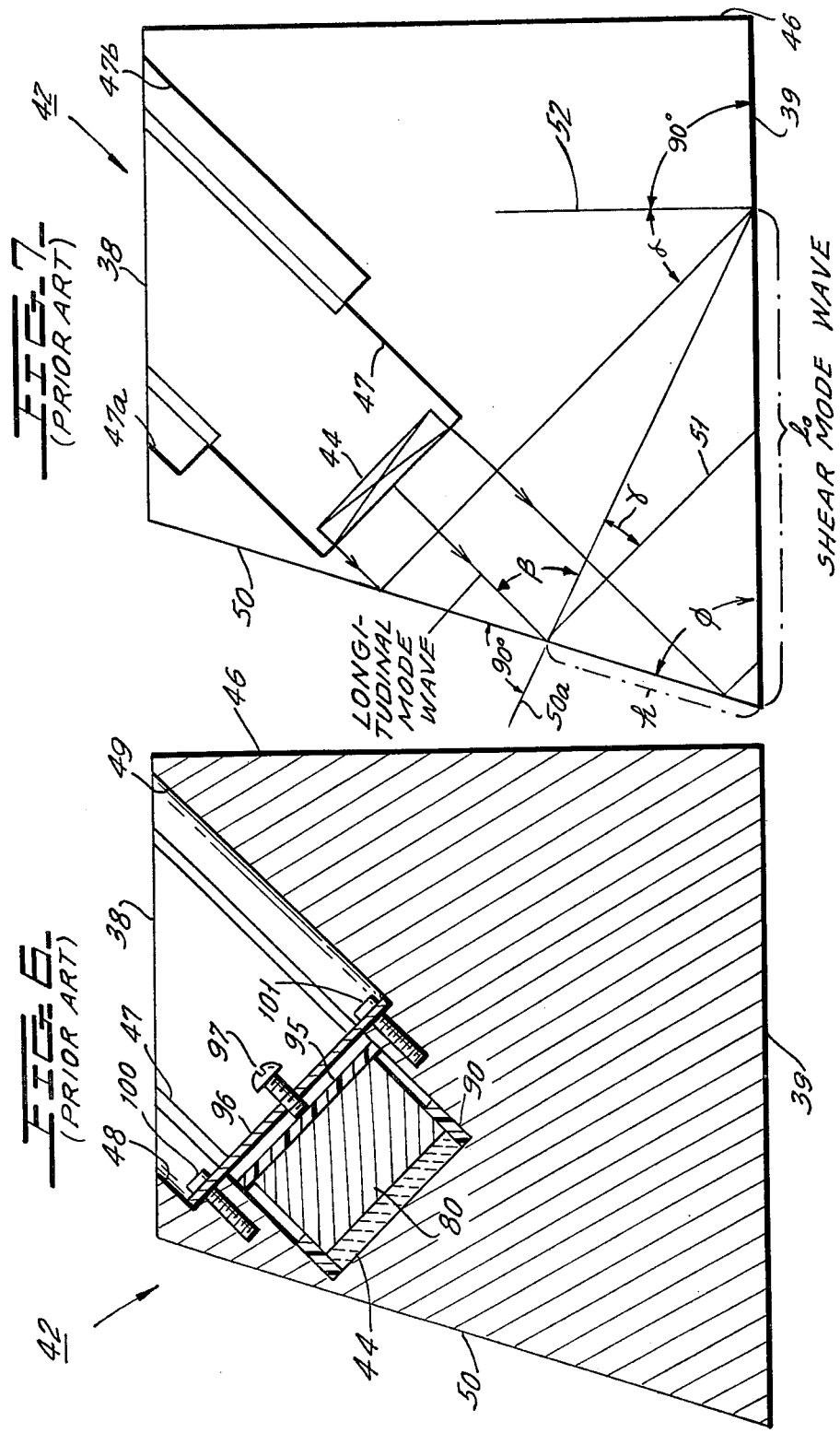

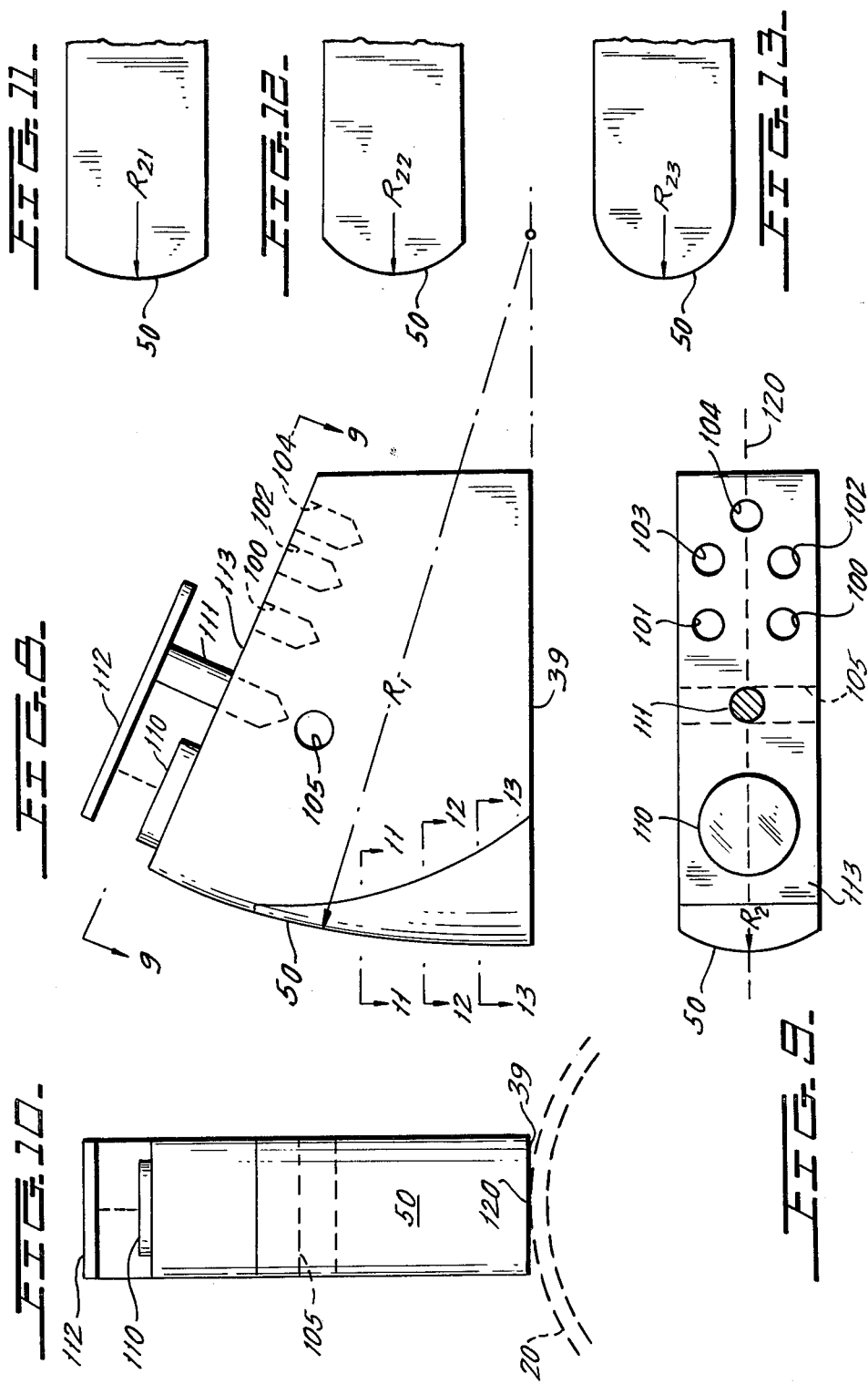

METAL TRANSDUCER HOUSING WITH FOCUSING SURFACE

RELATED APPLICATIONS

This application is related to my copending application Ser. No. 407,434, filed Aug. 12, 1982, entitled TRANSDUCER HAVING METAL HOUSING AND EMPLOYING MODE CONVERSION (M-9508).

BACKGROUND OF THE INVENTION

This invention relates to transducer housings which can be clamped to a surface into which sonic energy is to be exchanged with the housings, and more particularly relates to a metal transducer housing capable of being cast and which has a sonic lenticular mode conversion surface.

Transducer structures for flow monitoring equipment are known and are shown, for example, in U.S. Pat. Nos. 3,869,915, 3,987,674 and 4,373,401, all of which are in the name of Joseph Baumoel.

Application Ser. No. 407,434 referred to above discloses the advantages of a metallic transducer housing and the use of a mode conversion surface for converting longitudinal mode ultrasonic energy into shear mode ultrasonic energy which has a relatively low speed of propagation.

Metals such as zinc and brass are disclosed for the metallic housing. When using metals such as zinc and brass, it is necessary that the metals be processed in a manner that does not form large grains since a large grain structure interferes with the sonic conductivity of the metal. Thus, special treatment is needed and the metal cannot ordinarily be cast because the cast cooling process produces the undesired large grain structure. Therefore, the transducers must be machined to shape from rolled stock. The resulting transducer housing is expensive because of both the materials needed and their subsequent machining.

The problem of large grain size growth in metals such as brass, zinc or lead has been described in copending application Ser. No. 410,000, filed Aug. 20, 1982, entitled HIGHLY DAMPED TRANSDUCER STRUCTURE in connection with the manufacture of a damper having a sonically conductive interface with crystal. It is disclosed that in order to make this body sonically conductive, grain size must be reduced as by rolling. It is also disclosed that when the metals are in their β state they contain numerous grain boundary dislocations which render the material unsuitable for a sonic conduction function.

A further problem in the prior art metal transducer structure is that the flat mode conversion surface tends to defocus the ultrasonic energy put out over the length of the so-called "footprint" or region from which ultrasonic energy leaves the transducer housing and enters the conduit. This defocusing is caused by the limited number of wavelengths in the footprint and causes aperture dispersion.

Another problem which has been experienced with metallic transducers is that transducer coupling fluids or oils cannot be effectively used for coupling a metal transducer housing to a metal conduit pipe wall and they are coupled only where the transducer and pipe wall are in actual contact. This is because the sonic impedance of the metal bodies is poorly matched to the sonic impedance of the coupling fluid. As a result, the only energy which enters the pipe wall from the housing is that energy appearing along the line of intersection of the flat metal housing output surface and the circular outer diameter of the metal pipe wall.

High Q transducer crystals had been used for the transducer housing in the prior art. These crystals, however, have numerous resonance modes which are difficult to match for a broad band type system.

BRIEF SUMMARY OF THE INVENTION

In accordance with a first feature of the invention, a metal transducer employing mode conversion techniques is made of an aluminum-zinc alloy which is capable of being cast near to its final size and remains sonically conductive after casting.

More particularly, when aluminum is alloyed with zinc, the aluminum will limit the grain size which is produced in the solid solution. Since the aluminum in an aluminum-zinc alloy limits grain size, the alloy can be beneficially used as a transducer housing since it has substantial sonic conductivity as compared to other metals which will develop relatively large grain sizes when cast.

A preferable aluminum-zinc alloy employs 12% of aluminum by weight, which alloy is known as a ZA12 alloy. The alloy can be cast to any desired shape including those described in the above-described patents and applications. It can also be cast in the form of a transducer to be described having at least one lenticular surface. The cast transducer is preferably cast to a size larger than its final shape and therefore requires limited machining. Thus, the cost of the transducer structure is substantially reduced over those requiring machining and treatment to inhibit large grain growth.

A second feature of the invention is the use of a positive lenticular shape for the surface of a transducer which produces conversion between longitudinal mode sonic energy and shear mode sonic energy.

A first curvature applied to the mode conversion surface is hereinafter referred to as a cross-curvature which is one which curves on a radius which swings through an arc which is generally perpendicular to the direction in which sonic energy flows through the transducer housing. By producing the appropriate curvature, it is possible to cause the sonic energy to be focused along the line of contact between the output surface of the transducer housing and the metal pipe engaged thereby. The cross-curvature radius for the mode conversion system changes along the longitudinal length of the mode conversion surface since the focal point on the output transducer housing surface changes in distance from the associated mode conversion surface from which energy rays are reflected. Thus, the cross-curvature decreases in radius when progressing along the mode conversion surface, when moving from the transducer crystal toward the opposite end of the mode conversion surface.

This cross-curvature produces a number of advantages:

First, by focusing all energy on this output line, substantial energy can be applied to the conduit and a substantial increase is obtained in the signal-to-noise ratio for the system. For example, an increase greater than three times the ratio for a metal transducer employing a flat or non-lenticular mode conversion surface is obtained.

Secondly, when focusing all energy along the line of connection between the transducer housing output surface and the conduit to which it is connected, the sonic coupling medium, such as an oil or the like, between the output surface and the conduit is made more effective. It also makes practical the use of narrow optically flat areas of contact between the transducers and pipe to completely eliminate the need for coupling compounds which may evaporate at high temperature.

Third, the transducer crystal has a lower Q than was previously used. Thus, it is possible to use a transducer crystal made, for example, of lead metaniobate in place of the formerly used lead zirconium titanate (PZT5A). The lead metaniobate is relatively inexpensive and has a Q of about 15 as compared to a Q of 80 for the lead zirconium titanate. By employing a crystal of lower Q, there will be a broad-band, or fewer resonance modes so that it becomes much easier to match the crystal to the pipe and to other crystals of other transducers. A further advantage of the lower Q transducer crystal, particularly lead metaniobate, is that it has a curie temperature in excess of 400° C. and has relatively low capacitance.

A further advantage of the novel system is that the damper structure used to damp internal energy within the crystal can be relatively simple or can even be eliminated since a relatively high percentage of the energy will leave the crystal and enter the well-matched metal transducer housing.

The lenticular surface of the mode conversion surface of the metal transducer can have a further curvature therein which is hereinafter called a longitudinal curvature which is the curvature along a radius which sweeps in a plane which is generally parallel to the path taken by sonic energy through the crystal and is perpendicular to the direction of cross-curvature referred to above. The longitudinal curvature is a relatively slight curvature intended to adjust the phase velocity of the shear mode wave energy which propagates at the opposite ends of the so-called "footprint" of sonic energy which exits from the pipe wall and into the pipe interior. This longitudinal curvature tends to correct beam dispersion or "aperture dispersion" which was previously caused by the relatively low number of wavelengths in the footprint which tended to defocus or disperse the beam at the beginning and end of the footprint.

BRIEF DESCRIPTION OF THE DRAWINGS

FIG. 1 shows a transducer system of the prior art type.

FIG. 2 shows a transducer system of the prior art which employs mode conversion.

FIG. 3 is a cross-sectional view of a prior art metallic transducer housing of trapezohedron shape for producing mode conversion.

FIG. 4 is a view of FIG. 3 as seen from the line 4—4 in FIG. 3.

FIG. 5 is a cross-sectional view of a damper and crystal assembly which can be assembled with the housing of FIGS. 3 and 4.

FIG. 6 shows the assembly of the housing of FIGS. 3 and 4 and the damper and transducer crystal subassembly of FIG. 5.

FIG. 7 is a schematic view of FIG. 6 and contains notations useful in explaining the operation of the mode conversion system.

FIG. 8 is a side elevation view of a metallic transducer housing constructed in accordance with the invention, with a transducer crystal in place.

FIG. 9 is a view of FIG. 8 taken across the section line 9—9 in FIG. 8.

FIG. 10 is a side view of FIG. 8.

FIGS. 11, 12 and 13 are cross-sectional views of FIG. 8 taken across the section lines 11—11, 12—12 and 13—13, respectively, in FIG. 8 to illustrate the cross-curvature of the mode conversion surface of the transducer housing.

DETAILED DESCRIPTION OF THE DRAWINGS

The following detailed description of FIGS. 1 to 7 is taken in part from copending application Ser. No. 407,434 and will place the prior art in perspective before describing the invention shown in FIGS. 8 to 13.

A. Prior Art Employing Plastic Transducer Housing and Longitudinal Mode Operation Referring first to FIG. 1, there is shown therein the prior art arrangement of transducers in a system of the type such as that shown in U.S. Pat. No. 3,987,674. In this system, it is desired to measure the flow velocity of a material such as liquid within the conduit 20. A pair of transducers 21 and 22 are clamped to the outside surface of the conduit 20 and are axially displaced from one another. A suitable clamping means such as that shown in U.S. Pat. No. 4,373,401, referred to above, can be used to secure the transducers to the conduit 20.

Transducer devices 21 and 22 consist of housings 23 and 24, respectively, which contain transducer crystals 25 and 26, respectively. Crystals 25 and 26 are excited to produce output sonic pulse trains which propagate through housings 23 and 24 with longitudinal mode transmission. The rear surface of transducer crystals 25 and 26 are provided with dampers 27 and 28, respectively, as described in U.S. Pat. No. 3,987,674.

Transducer assemblies 21 and 22 alternate as transmitters and receivers, respectively, of ultrasonic energy. Initially, for example, transducer assembly 21 is the transmitter. The ray pattern shown in FIGS. 1 and 2 is for the case of transmission of energy from transducer 21 to transducer 22. A reverse pattern would exist for reverse transmission. Crystal 25 injects a longitudinal mode wave into housing 23, which propagates toward the pipe or conduit 20 to excite a shear mode wave in the wall of the conduit. Energy from the conduit wall enters the fluid or other contents within pipe 20 and passes through the pipe interior. The transmitted pulse is ultimately received by transducer crystal 26. A suitable electronic circuit (not shown) measures the transit time of the signal through the interior of conduit 20. Crystal 26 then returns a similar sonic signal which is received by the crystal 25 and the transit time is measured. The times for upstream and downstream transmission of the signals are then subtracted to produce a measure of the flow velocity of the fluid within the conduit 20.

The "footprint" of the sonic signal which is transmitted through the interior of conduit 20 is extremely long, as shown in FIG. 1. Thus, the axial location of the transducer assemblies 21 and 22 relative to one another is noncritical in regard to the effect of liquid refraction. This long footprint is obtained by adjusting the angle α of FIG. 1 such that the wave front of the longitudinal mode wave traveling parallel to line 30 reaches the wall of the conduit 20 at an angle such that the phase velocity of the longitudinal mode wave equals the shear mode velocity $V_{ps}$ in the pipe or conduit wall 20. As a result, the shear mode wave propagates axially along the wall of pipe 20 and acts as a new source of coherent signals which are introduced into the interior of conduit 20 and arrive, ultimately, at the receiving transducer location.

This wide beam arrangement has made possible extremely sensitive, yet rugged transducer systems which can be clamped to the exterior of a conduit without having to critically locate the transducers relative to one another or to adjust their positions relative to one another as temperature changes or as the conduit contents change. Moreover, the same transducer can be used for a wide variety of pipe materials and diameters. It is, however, necessary to choose materials for transducer bodies 23 and 24 of FIG. 1 which have longitudinal mode sonic velocities which are less than the shear mode velocity $V_{ps}$ of the conduit material. This is necessary so that the phase velocity of the sonic energy in the housings 23 and 24 can be adjusted to match the shear mode velocity of the pipe.

The material of conduit or pipe 20 is commonly steel. The shear mode velocity of steel is $126 \times 10^3$ inches/second. Thus, the material used for transducer housings 23 and 24 must have a longitudinal mode velocity substantially less than $126 \times 10^3$ inches/second. Since metals commonly have a longitudinal mode sonic velocity much higher than $126 \times 10^3$ inches/second, it has been necessary to use plastic materials for the transducer body. Common plastic materials, however, are not stable over wide temperature ranges and therefore cannot be used, for example, on steel pipe carrying hot fluids so that esoteric, expensive plastics were needed for these applications.

B. Prior Art Employing a Metal Transducer Housing and Mode Conversion

Application Ser. No. 407,434 describes a structure and process for injecting a relatively low shear mode velocity sonic wave from a transducer housing, which is preferably but not necessarily of metal, into a pipe wall which is preferably but not necessarily metal. As shown in FIG. 2, mode conversion transducer assemblies 40 and 41 are clamped to the surface of conduit 20. The mode conversion transducer assemblies 40 and 41 consist of housings 42 and 43, respectively, which have the shape of a trapezohedron. The bodies 42 and 43 receive transducer crystals 44 and 45, respectively, which may be backed by suitable dampers 44a and 45a, respectively. Moreover, the crystals 44 and 45 can be placed on the top surface of their housing bodies 42 and 43, with these surfaces at an appropriate angle so that the energy of crystals 44 and 45 propagates in the desired direction. Crystals 44 and 45 have been lead zirconium titanate, for example, which has a high Q and produces substantial output power with numerous resonance modes. Such crystals are relatively hard to match to one another to improve common mode drift effects.

Housings 42 and 43 have respective mode conversion reflection surfaces 50 and 51 which are arranged to receive the longitudinal mode wave output of transducer crystals 44 and 45, respectively, and to reflect a large percentage of this longitudinal mode energy as a shear mode wave which is directed toward and at an angle $\alpha$ to the surface of conduit 20. As will be later described in more detail, the mode conversion transducers 40 and 41 inject a shear mode sonic energy wave into conduit 20 which has a phase velocity approximately equal to the shear mode velocity $V_{ps}$ of the conduit 20 material.

By converting to shear mode energy within the housing 42, one can now select metals for the housing material since the shear mode velocity of metals having a suitable Poisson's ratio for efficient mode conversion will often have a lower shear mode velocity than that, for example, of steel. By way of example, housings 42 and 43 may be of brass which has a longitudinal mode velocity of $170 \times 10^3$ inches/second which is too high to be coupled to conduit 20 if it is made of steel. However, the shear mode velocity of brass is only $80 \times 10^3$ inches/second. Consequently, a brass transducer housing was disclosed for use in connection with an iron or steel conduit 20 in place of the more esoteric low longitudinal mode velocity plastics which were previously required.

FIGS. 3 and 4 show the housing 42 of the present invention in greater detail. The housing may be machined from particular metals. Brass which is finished with a nickel plate and unfinished zinc have been used successfully. The metal housing, however, had to be completely machined to size from rolled plate, rather than cast blanks, because the cooling which occurs with a casting process ordinarily produces grain sizes too large to make the metal body sonically conductive.

The metal housing of FIGS. 3 and 4 has the general shape of a trapezohedron and has flat parallel top and bottom surfaces 38 and 39, respectively, and non-parallel flat surfaces 50 (FIG. 3) and 46 which complete the trapezoidal outline of the housing. A transducer receiving opening 47 is machined into the top surface 38 and securement bracket openings 48 and 49 having tapped openings 47a and 47b, respectively, at their bases are provided as shown. Note that top surface 38 can directly receive a transducer crystal and, if so, the surface 38 would be sloped to be parallel to the bottom of opening 47. If opening 47 is used, transducer crystal 44 is appropriately seated on the bottom of opening 47 after the bottom of opening 47 has been satinized to ensure very close coupling between the lower surface of crystal 44 and the bottom of opening 47.

The flat surface 50 serves as the mode converting surface which converts a longitudinal mode sonic wave directed at its internal surface into a reflected shear mode wave and vice-versa of opening. The bottom 39 serves as the surface of the transducer which is ultimately coupled to a volume, such as a conduit 20, which is to receive energy from the transducer. Any desired well-known type of transducer element or crystal can be used. High Q crystal elements had been commonly used.

For purposes of illustration, one typical prior art brass transducer housing, which was built and tested and which employed the concept of the present invention, had a width of about 1.6", a length for surface 46 of about 4.37", a length for surface 39 of about 4.81" and a length for surface 38 of about 3.5". In order to ensure conversion from the longitudinal mode wave to the shear mode wave, and as shown in FIG. 7, the angle $\beta$ between the axis of opening 47 and a normal 50a to surface 50 is made to be 65°. This combination with a Poisson's ratio of the brass ensures conversion of a substantial portion of the longitudinal energy into shear mode energy. The shear mode energy then propagates in the direction of line 51 of FIG. 7 which is at an angle γ to the normal 50a which is 25.25°. Note that the angle α between the normal 52 to the direction of travel of the shear mode wave is 43.60°. The ultimate relationships between the various dimensions are determined by the following equations:

$$\sin\gamma = \frac{v_{cs}}{v_{cl}} \cdot \sin\beta \quad (1)$$

$$\sin\alpha = \frac{v_{cs}}{v_{ps}} \quad (2)$$

$$\phi = \alpha + \gamma \quad (3)$$

$$h = \frac{d}{\cos\beta} \quad (4)$$

$$l_o = \frac{h \cos\gamma}{\cos\alpha} = \frac{d \cos\gamma}{\cos\beta \cos\alpha} \quad (5)$$

In the above equations:

$v_{cs}$ is the shear mode velocity of the transducer body 42;

$v_{cl}$ is the longitudinal mode velocity of the transducer body 42;

$v_{ps}$ is the shear mode velocity of the conduit to which the transducer is connected;

h is the distance along face 50 from the bottom of the face to the point where the axis of opening 47 intersects the face;

$l_o$ is the length along the bottom surface 39 at which energy is injected into the pipe or conduit;

d is the diameter or width of the transducer crystal 44.

The prior art transducer crystal 44 is shown in FIGS. 2, 5, 6 and 7 as secured to the bottom of a suitable damper and mounting support structure. The damper and mounting support structure of FIG. 5 for the crystal body holds the crystal in place within the transducer housing and also receives and damps rearward-going energy put out from the rear surface of the transducer crystal. The adjoining surfaces of the crystal and housing are opticallly flat. Note that such dampers can be eliminated when using the present invention.

The damper consists of a brass body 80 which has a large plurality of conically tapered openings such as openings 81 and 82 therein which are packed as closely together as reasonably possible. The conical openings 81 and 82 have apices which form an angle of about 30° and any suitable length.

After machining and otherwise processing the damper structure 80, the conical openings 81 and 82 are filled with an epoxy having immersed therein small metal and plastic particles which serve as additional scattering centers, as shown in FIG. 5. A plastic ring 90 is then cemented to the outer periphery of crystal 44 and to the bottom outer periphery of damper 80 in order to secure the two together. A suitable coupling grease can be employed between the surfaces of crystal 44 and damper 80.

The face contact of crystal 44 is electrically connected by means (not shown) to the lead 91. Similarly, the rear electrode of crystal 44 is connected by means (not shown) to lead 92. Leads 91 and 92 are then connected to electrically accessible terminals 93 and 94, respectively, which are connected to the transducer driving and receiving circuits.

The top of damper 80 then receives a gasket 95 which is covered by a pressure disk 96. The pressure disk 96 is adapted to receive a pressure screw 97 which is threaded through support plate 98 which is bolted in place as shown in FIG. 6 by the bolts 100 and 101 which secure the assembly of FIG. 5 within the opening 47 in the housing 42.

In operation, and as shown in FIG. 6, when an electrical pulse is applied to terminals 93 and 94 of transducer crystal 44, the transducer puts out a high frequency longitudinal mode pulse. This longitudinal wave is injected into housing 42 and is intercepted by the interior wall of mode conversion surface 50. As shown in FIG. 7, the energy reflected from mode conversion surface 50 is at an angle β to the normal 50a and is in the form of a shear mode wave which has a velocity substantially less than the velocity of the longitudinal mode wave produced by crystal 44. This shear mode wave then exits along the length $l_o$ of surface 39 and enters the wall of pipe 20 (FIG. 2) with a phase velocity which is matched to the shear mode velocity of sonic energy in the pipe wall material. Consequently, there is an excellent impedance match between the transducer and the pipe so that there is excellent energy transfer with very sharp pulse signals being applied to the pipe wall and into the interior of the conduit.

C. The Novel Transducer Housing Metal and Manufacturing Process

In accordance with a first feature of the present invention, it has been found that the metallic material for the housings 42 and 43 of FIGS. 2, 3, 6 and 7 can be made of an aluminum-zinc alloy, which alloy is sonically conductive even when it is formed by a casting process. Thus, prior art metallic housings were disclosed as being of metals such as brass and zinc. These housings, however, had to be specially manufactured and treated in order to be sonically conductive since the metals disclosed tend to grow large grains which produce numerous grain boundary dislocations which inhibit sonic conduction through the metal coupler. In order to prevent the growth of these boundaries, the metals are commonly specially treated and then machined to their final size.

It has been found that aluminum, when alloyed with zinc, tends to inhibit large crystal growth. This inhibition is sufficient to inhibit the large crystal growth even when the aluminum-zinc alloy metal is cast to the shape required for the transducer housing, such as that of FIGS. 2, 3, 4, 6 and 7. While a wide range of aluminum-zinc alloys can be used, an alloy containing 12% of aluminum by weight is preferred since it is commercially available as a ZA12 alloy. As pointed out above, this material, which is commercially available, can be cast to the desired shape, with limited machining being necessary to bring the unit to final dimensions, drilling mounting holes, optically flattening, or satinizing surface portions which receive the transducer crystal and the like. Consequently, the transducer housing is less expensive than one made of brass or zinc rolled plate which must be machined to final form.

D. The Novel Lenticular Shape of the Mode Conversion Surface 50

In accordance with a second aspect of the invention, the surface 50 of the prior art transducer housing is modified in shape from the flat area disclosed in FIGS. 3, 6 and 7 to an area containing curvature in either or both a longitudinal direction and a cross-direction.

The novel transducer housing is shown in FIGS. 8 to 13. The material for the transducer housing is preferably an aluminum-zinc alloy, as stated previously, but can be of any metallic material which will still provide the advantages of the curvature of its mode conversion surface 50. The transducer housing of FIGS. 8 to 13 has a bottom flat surface 39 and is in the general shape of a rhomb as was the case of the prior art transducer, but is of slightly different rhomboid configuration.

When employing the aluminum-zinc alloy for the body of the transducer housing, less damping is necessary than for the prior art transducers while still producing an extremely sharp output signal and, if desired, damping can be eliminated. However, damping openings, such as openings 100 to 104, can be provided in the metal body, which openings can, for example, be filled with lead which is very lossy sonic material. A mounting opening 105 extends transversely through the housing and serves to scatter internal reflection of energy not transmitted to the pipe.

A transducer crystal 110 is suitably clamped against the surface 113 of the housing as by a clamping mechanism employing a post 111 and mounting plate 112. The angle of surface 113 relative to the vertical is appropriately chosen so that energy from crystal 110 is directed in the proper angle toward the mode conversion surface 50. The engaging surfaces of the crystal and housing are preferably optically flat to eliminate the need for a limited-life coupling compound.

The bottom surface 39 of the transducer is a flat surface. It, therefore, engages the outer surface of a round conduit 20 along a straight line shown by the line 120 in FIGS. 9 and 10. Since both the transducer housing 50 and conduit 20 are of metal, the use of coupling grease in the gap between the surface 39 of housing 50 and the conduit 20 will not couple energy effectively because of the wide difference in the sonic impedance in the metal and in the coupling grease. Consequently, most energy from the transducer housing 50, which enters the conduit 20, enters at the line of engagement 120. This line of engagement, however, contains only a small fraction of the total energy available from the crystal 110.

In accordance with one aspect of the present invention, the mode conversion surface 50 is contoured to have a positive cross-curvature which acts as a lens and tends to focus the shear mode wave energy reflected from surface 50 along the line of intersection 120 between the housing 50 and the conduit 20.

In order to focus the energy along the entire line 120, it is necessary to gradually increase the cross-curvature of surface 50 along the length of the surface proceeding from the top of surface 50 (adjacent crystal 110) toward the bottom of surface 50.

By way of example, in a particular transducer housing made of an aluminum-zinc alloy having 12% aluminum, surface 50 had a longitudinal length of 1 31/32" and a width of 1". Surface 113 formed an angle of 25.3° relative to the bottom surface 39. At a point about half way along the length of surface 50, shown in section 11—11 in FIG. 8 and in FIG. 11, the curvature $R_{21}$ was 1.79". At a point one quarter the length of surface 50 from the bottom of the transducer housing, indicated by section line 12—12 in FIG. 8, and in FIG. 12, the radius of curvature $R_{22}$ was 1.28". At the location near the bottom of surface 50 in FIG. 8, indicated by section line 13—13 in FIG. 8, and shown in FIG. 13, the radius of curvature was 0.093". Note that the curvature of surface 50 may be appropriately cast from a mold formed with this curvature, or may be machined with the curvature extending gradually from point to point in a smooth, well-defined manner. The use of the above dimensions produced focusing of the energy of transducer crystal 110 along the line 120, where the transducer engaged a round conduit.

The novel cross-curvature lens type of action of surface 50 described above causes a significant increase in the signal-to-noise ratio is produced for the system. By way of example, the signal-to-noise ratio is improved over that of the prior art by a factor in excess of 3.

The transducer crystal employed with the present invention preferably is a relatively inexpensive crystal having a low Q. By way of example, the crystal 110 can be of lead, metaniobate rather than lead zirconium titanate. Lead metaniobate transducers have a Q of about 15 compared to a Q of about 80 for the lead zirconium titanate. By using a low Q transducer crystal, there are fewer resonance modes so that the entire system becomes much easier to match and broad-banded and extremely sharp and well-defined output pulses can be produced from the transducer housing into the conduit 20.

The use of the lead metaniobate crystal is also preferable to other ceramics since it has a very high curie temperature which is greater than 400° C. and a relatively low capacitance. Moreover, simpler damper structures can be used than with the higher Q transducer crystals and, in some cases, no damper is required.

In accordance with a further feature of the invention, a second positive curvature is employed for surface 50 which is perpendicular to the cross-curvature previously described. The second curvature can be used with or without the cross-curvature and is the curvature of the surface 50 over the radius $R_1$ shown in FIG. 8. This radius of curvature in the transducer housing previously disclosed for FIGS. 8 to 13 can be about 15.681".

The longitudinal curvature of the surface 50 is used to correct "aperture dispersion" which is produced when the radius $R_1$ is infinite. Thus, when the radius of longitudinal curvature is infinite (and with or without the cross-curvature), there is some propagation curvature or defocusing of the energy at the beginning of the footprint. By longitudinally curving the surface on a relatively large radius, this aperture dispersion effect is substantially corrected.

In the above there has been described both a longitudinal curvature and a cross-curvature for the surface 50. When both are employed, the surface will have a lenticular configuration. In this lenticular configuration, the cross-curvature is, as previously defined, a curvature on a radius which sweeps in a plane which is generally perpendicular to the plane of travel of sonic energy from crystal 110 to the surface 39. The longitudinal curvature of surface 50 is defined as the curvature on the radius $R_1$ which sweeps in a plane which is generally parallel to the plane of propagation of sonic energy through the housing. Note that mode conversion surface 50 can employ either one or both of the longitudinal and cross-curvatures described above and further that the metal transducer body can be of any metal, although it is preferred to employ the aluminum-zinc alloy so that the body can be cast.

Although the present invention has been described in connection with a preferred embodiment thereof, many variations and modifications will now become apparent to those skilled in the art. It is preferred, therefore, that the present invention be limited not by the specific disclosure herein, but only by the appended claims.

What is claimed is:

1. A transducer comprising, in combination, a transducer element and a metal housing having the shape of a trapezohedron; said trapezohedron having a first planar edge surface defining an output energy surface and a second edge surface defining a mode conversion surface by internal reflection of a longitudinal mode wave; said first and second planar surfaces intersecting one another with an internal angle $\phi$; said transducer element being a flat, thin element coupled to said metal housing and disposed in a plane which has a normal which forms an internal angle $\beta$ with respect to a normal to said second surface; longitudinal sonic energy from said transducer element being reflected from the interior of said second surface and being converted into shear mode sonic energy which is directed away from said second surface in a direction which forms an internal angle $\alpha$ with respect to a normal to said second planar surface and on the side of said normal away from the side thereof defining said angle $\beta$; wherein $\phi = \alpha + \gamma$ is the internal angle between the direction of propagation of said shear mode wave and a normal to said first planar surface; and $\sin \gamma = (v_{cs}/v_{cl}) \sin \beta$ wherein $v_{cs}$ is the shear mode velocity of said metal and $v_{cl}$ is the longitudinal mode velocity of said metal; wherein the improvement comprises forming a variable positive cross-curvature along the length of said second surface to define a lens for focusing said shear mode sonic energy onto a line extending along said output energy surface.

2. A transducer comprising, in combination, a transducer element and a metal housing having the shape of a trapezohedron; said trapezohedron having a first planar edge surface defining an output energy surface and a second edge surface defining a mode conversion surface by internal reflection of a longitudinal mode wave; said first and second planar surfaces intersecting one another with an internal angle $\phi$; said transducer element being a flat, thin element coupled to said metal housing and disposed in a plane which has a normal which forms an internal angle $\beta$ with respect to a normal to said second surface; longitudinal sonic energy from said transducer element being reflected from the interior of said second surface and being converted into shear mode sonic energy which is directed away from said second surface in a direction which forms an internal angle $\alpha$ with respect to a normal to said second planar surface and on the side of said normal away from the side thereof defining said angle $\beta$; wherein $\phi = \alpha + \gamma$ is the internal angle between the direction of propagation of said shear mode wave and a normal to said first planar surface; and $\sin \gamma = (v_{cs}/v_{cl}) \sin \beta$ wherein $v_{cs}$ is the shear mode velocity of said metal and $v_{cl}$ is the longitudinal mode velocity of said metal; wherein the improvement comprises forming a positive longitudinal curvature over the length of said second surface to reduce aperture dispersion effects.

3. The transducer of claim 1 or 2 wherein said metal housing is an alloy of aluminum and zinc.

4. The transducer of claim 1 wherein said second surface has a positive longitudinal curvature over the length of said second surface to reduce aperture dispersion effects, thereby to produce a lenticular shape for said second surface.

5. The transducer of claim 1 or 2, wherein said second surface is coupled to a hollow elongated metal conduit; said metal conduit having a characteristic shear mode velocity $v_{ps}$ and wherein $\sin \alpha = (v_{cs}/v_{ps})$.

6. The transducer of claim 1 wherein said transducer element has a relatively low Q of about 15.

7. A mode conversion transducer comprising a metal body having an output surface adapted to engage an output metal body along a relatively narrow line of engagement, a mode conversion surface adapted to receive longitudinal mode sonic energy from a transducer source and to internally convert said mode sonic energy into shear mode sonic energy and to direct said shear mode sonic energy toward said output surface; wherein the improvement comprises forming said mode conversion surface with a positive cross-curvature to focus said shear mode sonic energy onto a relatively narrow line along said output surface, which corresponds to said relatively narrow line of engagement.

8. The transducer of claim 7 which further includes a transducer crystal fixed to said metal body to serve as a source of longitudinal mode sonic energy which it applied to said mode conversion surface; said transducer crystal having a low Q.

9. The transducer of claim 8 wherein said transducer crystal is of lead metaniobate.

10. A mode conversion transducer comprising a metal body having an output surface adapted to engage an output metal body along a relatively narrow line of engagement, a mode conversion surface adapted to receive longitudinal mode sonic energy from a transducer source and to internally convert said mode sonic energy into shear mode sonic energy and to direct said shear mode sonic energy toward said output surface; wherein the improvement comprises forming said mode conversion surface with a positive longitudinal curvature to reduce defocusing of shear mode sonic energy along the length of said output surface.

11. The transducer of claim 7 wherein said mode conversion surface further has a positive longitudinal curvature to reduce defocusing of shear mode sonic energy along the length of said output surface.

12. The transducer of claim 7, 10 or 11 wherein said metal is an aluminum-zinc alloy formed by the process of casting.

* * * * *